US011099801B2

(12) United States Patent
Sugumi et al.

(10) Patent No.: US 11,099,801 B2
(45) Date of Patent: Aug. 24, 2021

(54) DISPLAY SYSTEM AND PROGRAM

(71) Applicant: EIZO Corporation, Hakusan (JP)

(72) Inventors: Masahiro Sugumi, Hakusan (JP); Airi Kurokawa, Hakusan (JP); Hideaki Hashimoto, Hakusan (JP); Tatsuya Nakamura, Hakusan (JP); Wei Song, Hakusan (JP)

(73) Assignee: EIZO Corporation, Hakusan (JP)

( * ) Notice: Subject to any disclaimer, the term of this patent is extended or adjusted under 35 U.S.C. 154(b) by 0 days.

(21) Appl. No.: 16/981,419

(22) PCT Filed: Mar. 19, 2019

(86) PCT No.: PCT/JP2019/011311
§ 371 (c)(1),
(2) Date: Sep. 16, 2020

(87) PCT Pub. No.: WO2019/188531
PCT Pub. Date: Oct. 3, 2019

(65) Prior Publication Data
US 2021/0011679 A1  Jan. 14, 2021

(30) Foreign Application Priority Data
Mar. 28, 2018 (JP) .............................. JP2018-062207

(51) Int. Cl.
*G06F 3/14* (2006.01)
(52) U.S. Cl.
CPC .......... *G06F 3/1438* (2013.01); *G06F 3/1446* (2013.01); *G09G 2370/20* (2013.01)
(58) Field of Classification Search
CPC .. G06F 3/1438; G06F 3/1446; G09G 2370/20
(Continued)

(56) References Cited

U.S. PATENT DOCUMENTS 7,227,510 B2 *  6/2007  Mayer, III ............ G06F 3/1446
                                                           345/1.1
10,073,542 B2 *  9/2018  Kato ....................... H04M 3/56
(Continued)

FOREIGN PATENT DOCUMENTS

JP  H10-214070 A  8/1998
JP  2001-067055 A  3/2001
(Continued)

OTHER PUBLICATIONS

International Search Report dated Jun. 11, 2019 in corresponding application No. PCT/JP2019/011311; 6 pgs.
(Continued)

*Primary Examiner* — Tom V Sheng
(74) *Attorney, Agent, or Firm* — Maier & Maier, PLLC

(57) ABSTRACT

The present invention provides a display system configured to control a plurality of display devices by combining a plurality of information processing devices and the display devices, even if the display system includes a display device incapable of communicating a switch signal with all of the information processing devices.

The present invention provides a display system comprising: first and second information processing devices; and first and second display devices, wherein the first and second display devices are configured to perform extended display with respect to one of an image output from the first information processing device and an image output from the second information processing device, the second information processing device is configured to output a second switch signal for switching an image displayed on the first display device to the first display device, and the first information processing device is configured to, when the second switch signal is output from the second information processing device to the first display device and the image displayed on the first display device is switched, output a
(Continued)

first switch signal for switching an image displayed on the second display device to the second display device.

14 Claims, 19 Drawing Sheets

(58) Field of Classification Search
USPC .......................................................... 345/1.2
See application file for complete search history.

(56) References Cited

U.S. PATENT DOCUMENTS

| | | | |
|---|---|---|---|
| 10,474,414 B2 * | 11/2019 | Ogawara | H04N 9/3147 |
| 2002/0008675 A1 * | 1/2002 | Mayer, III | H04N 9/12 |
| | | | 345/4 |
| 2003/0227423 A1 | 12/2003 | Arai et al. | |
| 2007/0297064 A1 * | 12/2007 | Watanabe | B60K 37/06 |
| | | | 359/630 |
| 2008/0036790 A1 * | 2/2008 | Ishiyama | G09G 5/36 |
| | | | 345/642 |
| 2009/0028402 A1 | 1/2009 | Ando | |
| 2016/0188274 A1 * | 6/2016 | Chen | G06F 3/04886 |
| | | | 345/2.1 |
| 2019/0373211 A1 * | 12/2019 | Chen | H04N 5/268 |
| 2020/0409646 A1 * | 12/2020 | Sugumi | G06F 3/1423 |

FOREIGN PATENT DOCUMENTS

| | | |
|---|---|---|
| JP | 2002-189542 A | 7/2002 |
| JP | 2003-210404 A | 7/2003 |
| JP | 2004-029046 A | 1/2004 |
| JP | 2004-070635 A | 3/2004 |
| JP | 2006-309052 A | 11/2006 |
| JP | 2007-310061 A | 11/2007 |
| JP | 2010-117495 A | 5/2010 |
| WO | 2007/099816 A1 | 9/2007 |
| WO | 2014/181420 A1 | 11/2014 |

OTHER PUBLICATIONS

Japanese Notice of Reason for Refusal dated Sep. 18, 2018 in corresponding application No. 2018-062207; 6 pgs.

* cited by examiner

DISPLAY SYSTEM AND PROGRAM

TECHNICAL FIELD

The present invention relates to a display system that combines multiple display devices and multiple Information processing devices.

BACKGROUND ART

There is known a display system in which a plurality of information processing devices are connected to a display device and images are displayed on the display device. For example, in a hospital, a plurality of information processing devices are respectively connected to a plurality of display devices, and the image displayed on the display devices is switched from the image of one information processing device to the image of another information processing device according to situations. For example, in a case that one information processing device is configured to connect to the server of hospital X and another information processing device is configured to connect to the server of hospital Y, the doctors switch the image displayed on the display device from the image of the one information processing device to the image of another information processing device to compare the images stored in the servers of hospitals X and Y.

Patent literature 1 discloses a workstation switching device configured to switch the image displayed on the display device among the images of workstations by only operating a mouse in addition to operating a mechanical switch and a keyboard.

CITATION LIST

Patent Literature

[Patent Literature 1] Japanese Unexamined Patent Application Publication No. 2002-189542

SUMMARY OF INVENTION

Problems to be Solved by the Invention

The present invention provides a display system configured to control a plurality of display devices by combining a plurarity of information processing devices and the display devices, even if the display system includes a display device incapable of communicating a switch signal with all of the information processing devices.

Solution to Problem

Various embodiments of the present invention are illustrated below. The embodiments shown below can be combined.

The present invention provides a display system comprising: first and second information processing devices; and first and second display devices, wherein the first and second display devices are configured to perform extended display with respect to one of an image output from the first information processing device and an image output from the second information processing device, the second information processing device is configured to output a second switch signal for switching an image displayed on the first display device to the first display device, and the first information processing device is configured to, when the second switch signal is output from the second information processing device to the first display device and the image displayed on the first display device is switched, output a first switch signal for switching an image displayed on the second display device to the second display device.

In the present invention, the second information processing device is configured to output the second switch signal for switching the image displayed on the first display device to the first display device. Then, the first information processing device is configured to output the first switch signal for switching the image displayed on the second display device to the second display device according to the second switch signal. Thus, even if the second display device and the second information processing device cannot communicate the switch signal with one another, the display system can control the display devices.

Various embodiments of the present invention are illustrated below. The embodiments shown below can be combined.

Preferably, the first information processing device, when the second switch signal is output from the second information processing device to the first display device and the image displayed on the first display device is switched, outputs the first switch signal to the second display so that the second display displays the image output from the first information processing device.

Preferably, the first and second displays include video signal communication parts respectively, the video signal communication parts are configured to communicate a video signal with between the first and second information processing devices, and the first information processing device is configured to detect, via the video signal communication part of the first display device, whether the image displayed on the first display device has been switched.

Preferably, the first and second display devices include switch signal communication parts respectively, the switch signal communication parts are configured to communicate the first switch signal or the second switch signal with at least one of the first and second information processing device, and the first information processing device is configured to detect, via the switch signal communication part of the first display device, whether the image displayed on the first display device has been switched.

Preferably, the first display device includes a switch signal transfer part, the switch signal transfer part is configured to transfer the second switch signal, input from the second information processing device to the first display device, to the first information processing device, or output an output signal to the first information processing device when the second switch signal is input from the second information processing device to the first display device, the output signal indicating that the second switch signal is input from the second information processing device to the first display device, and the first information processing device outputs the first switch signal to the second display device when the first information processing device receives the second switch signal or the output signal from the switch signal transfer part.

Preferably, the display system further comprises: an operation device configured to operate one of the first and second information processing devices that outputs the image to the first and second display devices, wherein the first information processing device is configured to detect whether the image displayed on the first display device has been switched by detecting that the operation device has switched to a state in which the operation device is capable of operating the first information processing device.

Preferably, the first and second display devices include switch signal communication parts respectively, the switch signal communication parts are configured to communicate the first switch signal or the second switch signal with at least one of the first and second information processing device, the switch signal communication part of the first display device is configured to communicate with the first and second information processing devices, the switch signal communication part of the second display device is configured to communicate with the first information processing device, the first switch processing, which switches the image displayed on the second display device from an image of the first information processing device to an image of the second information processing device, is executed when the first information processing device outputs a third switch signal to the first and second display devices, and the second switch processing, which switches the image displayed on the first display device from the image of the second information processing device to the image of the first information processing device, is executed when the first information processing device outputs the first switch signal to the second display device after the first display device receives the second switch signal from the second information processing device.

Preferably, the display system further comprises an operation device configured to operate one of the first and second information processing devices that outputs the image to the first and second display devices.

Preferably, the operation device is connected to the first display device.

Preferably, the operation device is configured to indicate a pointing position on the first and second display devices.

Preferably, the display system further comprises: a detector configured to, when the image is displayed on the first and second display devices, detect whether the pointing position is positioned on a switch area arranged in a direction perpendicular to a direction in which the first and second display devices are arranged, wherein the first switch processing or the second switch processing is executed when the detector detects the pointing position on the switch area.

Preferably, the first and second information processing devices include display switchers respectively, each of the display switchers displays information on at least one of the first and second display devices, the information indicating which image output from the first information processing device or the second information processing device is displayed on the first and second display devices.

Preferably, the first display device or the second display device is configured to display an electrical health record.

Another aspect of the present embodiments provides a program causing a computer to function as a controller that controls a display system including first and second information processing devices and first and second display devices, the first and second display devices being configured to perform extended display with respect to one of an image output from the first information processing device and an image output from the second information processing device, the second information processing device being configured to output a second switch signal for switching an image displayed on the first display device to the first display device, the program comprising: outputting, when the second switch signal is output from the second information processing device to the first display device and the image displayed on the first display device is switched, a first switch signal for switching an image displayed on the second display device from the first information processing device to the second display device.

DESCRIPTION OF EMBODIMENTS

Hereinafter, the embodiments of the present invention will be described with reference to the drawings. The various features shown in the embodiments below can be combined.

1. First Embodiment 1-1. Display System 10

Figure 1:
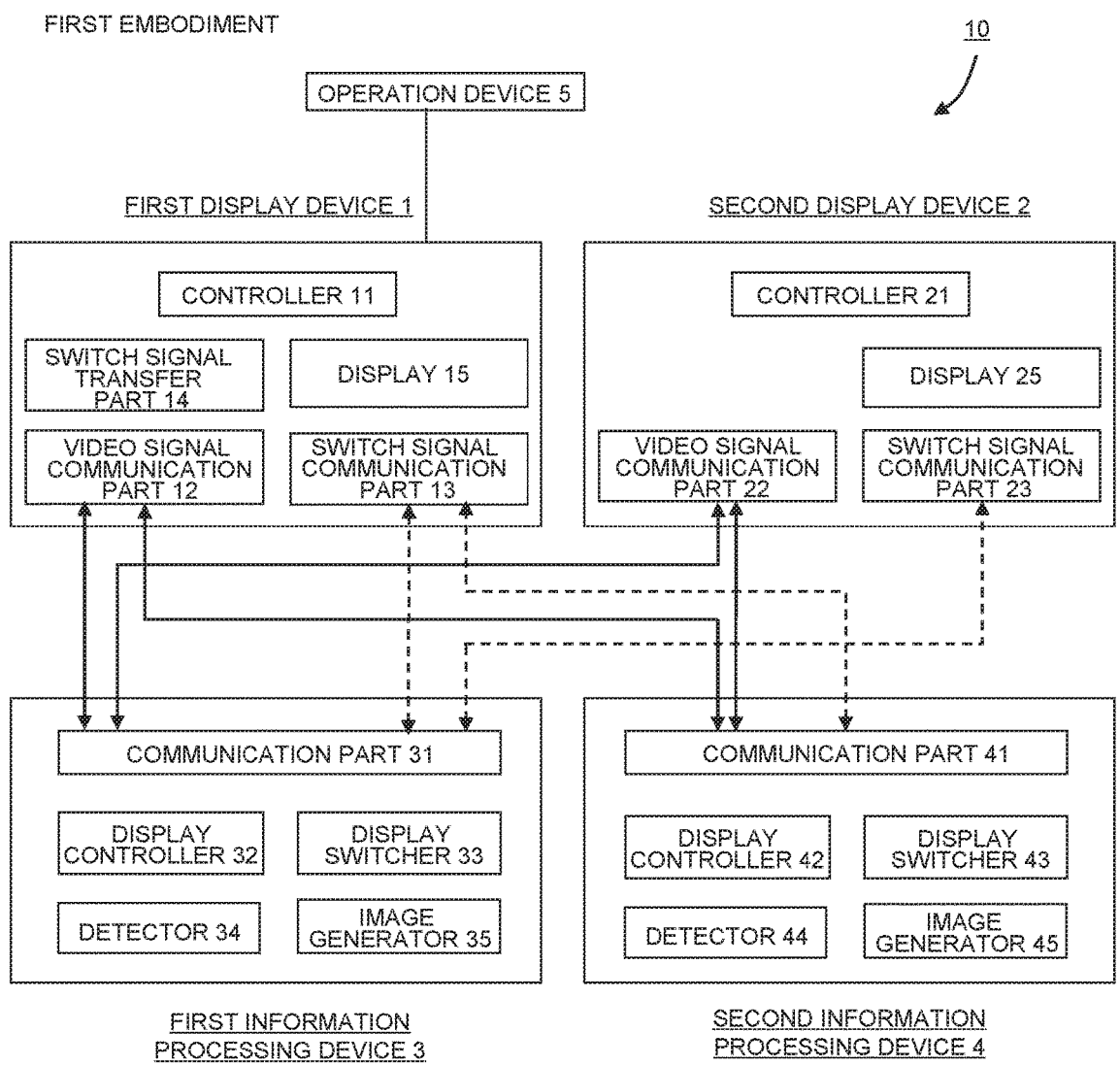
FIG. 1 is a functional block diagram showing a configuration of a display system 10 according to the first embodiment of the present invention.

The display system 10, according to the first embodiment of the present invention, will be described with reference to FIG. 1. As shown in FIG. 1, the display system 10 includes first and second information processing devices 3 and 4, and first and second display devices 1 and 2.

The first and second display devices 1 and 2 are configured to perform extended display with respect to an image output from the first information processing device 3 or an image output from the second information processing device 4. The second information processing device 4 is configured to output a second switch signal for switching an image displayed on the first display device 1, to the first display device 1. Further, the first information processing device 3 is configured to output a first switch signal for switching an image displayed on the second display device 2, to the second display device 2 according to the second switch signal. Details of configurations of the embodiment will be described below.

<First Information Processing Device 3>

The first information processing device 3 includes a communication part 31, a display controller 32, a display switcher 33, a detector 34, and an image generator 35.

The communication part 31 communicates various signals with the first and second display devices 1 and 2. The image generator 35 generates various image data. In this embodiment, image data generated by the first information processing device 3 is defined as a first image, and image data generated by the second information processing device 4 is defined as a second image. Here, the image data includes data corresponding to a still image and a moving image. The display controller 32 is configured to perform the extended display with respect to the image generated by the image generator 35 on the first and second display devices 1 and 2. The display switcher 33 switches the image displayed on the first and second display devices 1 and 2 in the extended display manner. In this embodiment, the display switcher 33 generates a switch signal for switching the image, which is displayed on the first and second display devices 1 and 2 in the extended display manner, from the first image to the second image. When the image is displayed on the first and second display devices 1 and 2 in the extended display manner, the detector 34 detects whether a pointing position PP is positioned on a switch area SR arranged in a direction perpendicular to a direction in which the first and second display devices 1 and 2 are arranged. Details of the detector 34 will be described later.

<Second Information Processing Device 4>

The second information processing device 4 includes a communication part 41, a display controller 42, a display switcher 43, a detector 44, and an image generator 45. Since the functions of the communication part 41, the display controller 42, the display switcher 43, the detector 44 and the image generator 45 are the same as the communication part 31, the display controller 32, the display switcher 33, the detector 34, and the image generator 35 of the first information processing device 3, and thus details of the functions are omitted.

<First Display Device 1>

The first display device 1 includes a controller 11, a video signal communication part 12, a switch signal communication part 13, a switch signal transfer part 14, and a display 15.

The controller 11, which corresponds to a CPU, for example, reads a program stored in a memory (not shown) and executes various arithmetic processing. The video signal communication part 12 is configured to communicate a video signal with the first and second information processing devices 3 and 4. Here, the video signal is an electric signal of an image and is used for communications of image data. In the first embodiment, the video signal communication part 12 is configured to communicate with the communication part 31 of the first information processing device 3 and with the communication part 41 of the second information processing device 4. The switch signal communication part 13 communicates various switch signals with at least one information processing device. In the first embodiment, the switch signal communication part 13 is configured to communicate with the communication part 31 of the first information processing device 3 and with the communication part 41 of the second information processing device 4. Further, the switch signal is transmitted and received between the first display device 1 and the first and second information processing devices 3 and 4 through the switch signal communication part 13.

The video signal communication part 12 and the switch signal communication part 13 are connected to the communication part 31 by wire or wireless.

When the switch signal transfer part 14 transfers the switch signal, input from the second information processing device 4, to the first information processing device 3, or when the switch signal is input from the second information processing device 4 to the switch signal transfer part 14, the switch signal transfer part 14 outputs a signal, indicating that the switch signal is input, to the first information processing device 3. The display 15 is configured to display input image data as the image, and the display 15 corresponds to, for example, a liquid crystal display, an organic EL display, a touch panel display, and an electronic paper.

Further, an operation device 5 is connected to the first display device 1. In this embodiment, the operation device 5 is configured to operate one of the first and second information processing devices 3 and 4 that outputs the image to the first and second display devices 1 and 2. Specifically, when the image displayed on the first display device 1 and the second display device 2 in the extended display manner is the first image, the operation device 5 is capable of operating the first information processing device 3. When the image displayed on the first and second display devices 1 and 2 in the extended display manner is the second image, the operation device 5 is capable of operating the second information processing device 4. In addition, the operation device 5 is configured to indicate the pointing position PP (see FIG. 3) on the first and second display devices 1 and 2.

<Second Display Device 2>

The second display device 2 includes a controller 21, a video signal communication part 22, a switch signal communication part 23, and a display 25. The functions of the controller 21, the video signal communication part 22, the switch signal communication part 23, and the display 25 are the same as those of the controller 11, the video signal communication part 12, the switch signal communication part 13, and the display 15, and thus details of the functions are omitted.

In the present embodiment, the switch signal communication part 23 of the second display device 2 is configured to communicate with the communication part 31 of the first information processing device 3, but cannot communicate with the communication part 41 of the second information processing device 4. The present embodiment assumes a case where the switch signal communication part 23 is a USB port, the second display device 2 has only one USB port, and the second display device 2 can be connected to only one information processing device.

Each of the above components may be realized by software or hardware. When realized by software, various functions can be realized by the CPU executing programs. The program may be stored in built-in memory or a non-transitory readable medium by a computer. Alternatively, the above functions are realized by reading the program stored in external memory using so-called cloud computing. When realized by hardware, the above functions can be performed by various circuits such as ASIC, FPGA, or DRP. The present embodiment deals with various information and concepts including this information, and the various information is a bit group of binary numbers having 0 or 1, and the various information is represented according to the level of signal value. And in the present embodiment, communications and calculations can be executed according to configurations of the above software and hardware.

1-2. Flowchart of First Embodiment

Next, the processing executed by the display system 10 will be described with reference to FIGS. 2 to 8.

Figure 3:
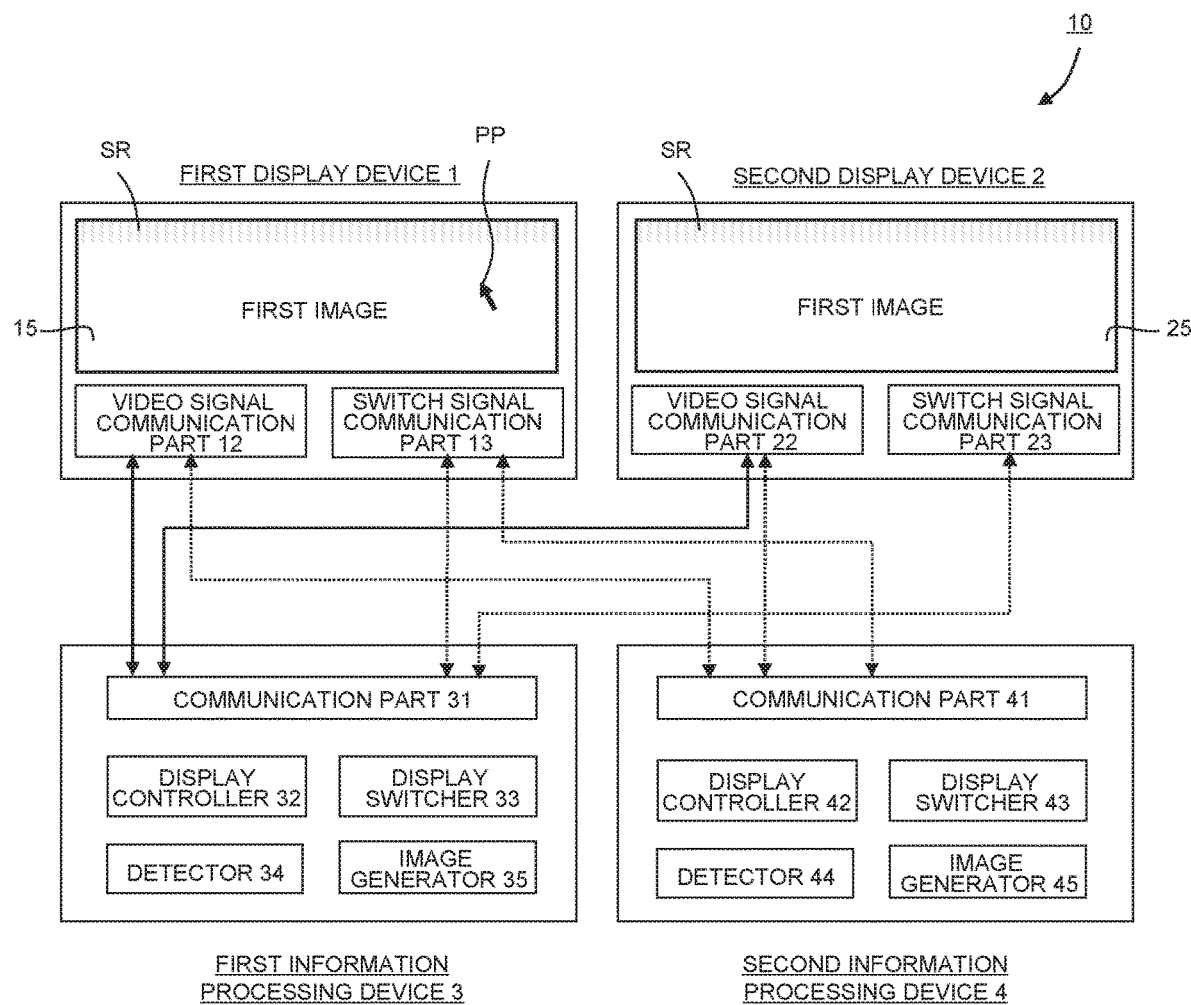
FIG. 3 is a schematic diagram showing a state that a first image is displayed on first and second display devices 1 and 2 in an extended display manner.

In S1, the first and second display devices 1 and 2 included in the display system 10 perform the extended display with respect to the image (the first image) output from the first information processing device 3. This corresponds to FIG. 3. Here, in the present embodiment, when the image is displayed on the first and second display devices 1 and 2 in the extended display manner, the switch area SR is arranged in a direction perpendicular to a direction in which the first and second display devices 1 and 2 are arranged. In the example of FIG. 3, the switch area SR is arranged in a vertical direction corresponding to the direction perpendicular to the direction (horizontal direction) in which the first and second display devices 1 and 2 are arranged. The reason for the switch area SR arranged in the vertical direction is to suppress unnecessary switch processing when the pointing position is moved on the first and second display devices 1 and 2 with the operation device 5. The position, where the switch area SR is arranged, is not particularly limited, and the switch area SR may be arranged in an arbitrary area. Further, the switch area SR may be a virtual area, may be arranged on the first image, or may be highlighted when the pointing position PP overlaps on the switch area SR.

Figure 2:
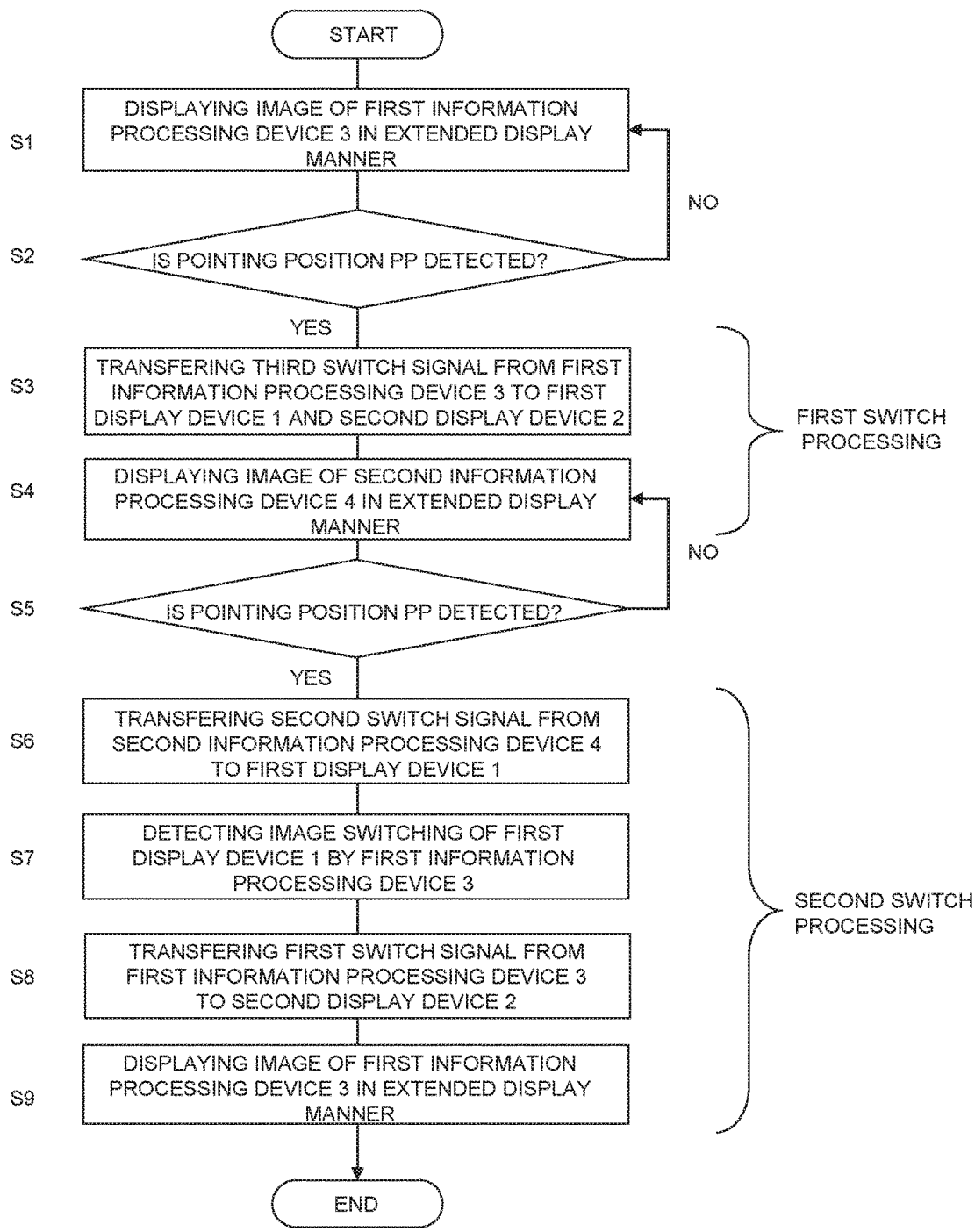
FIG. 2 is a flowchart showing processing of the display system 10 according to the first embodiment.
Figure 4:
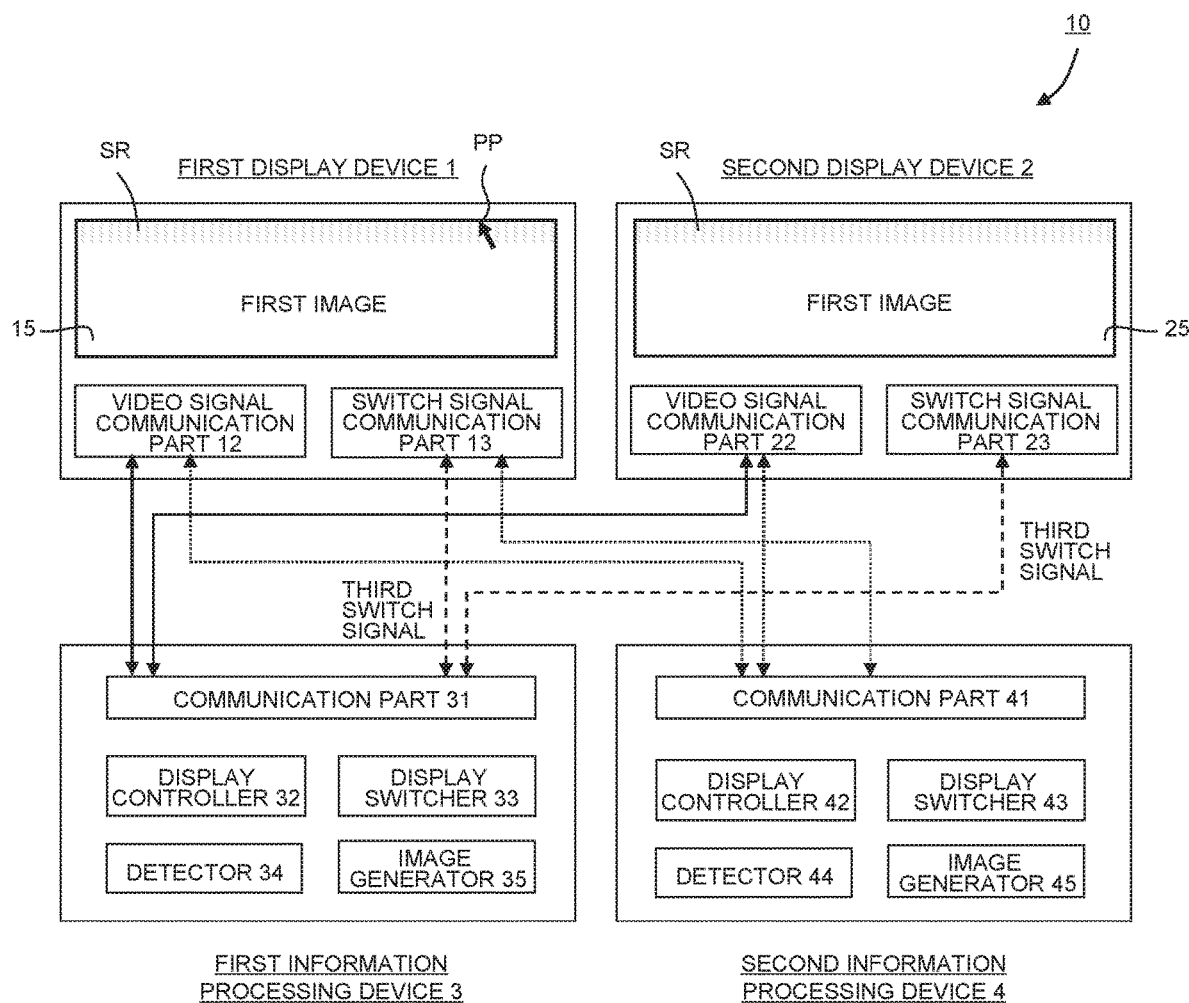
FIG. 4 is a schematic diagram showing a state that the first information processing device 3 outputs a third switch signal to the first display device 1 and the second display device 2. Here, the third switch signal is a signal for switching an image displayed on the first display device 1 or the second display device 2 to a second image.

Next, as shown in FIG. 4, when the operation device 5 is operated to move the pointing position PP into the switch area SR, the detector 34 detects that the pointing position PP is positioned on the switch area SR in S2 of FIG. 2. Then, when the pointing position PP is detected by the detector 34, the display system 10 starts to execute the first switch processing. When the detector 34 does not detect the presence of the pointing position PP on the switch area SR, the processing returns to S1.

Next, in S3, a third switch signal is transmitted from first information processing device 3 to the first and second display devices 1 and 2 as shown in FIG. 4. Here, the third switch signal is a signal for switching the image, displayed on the first display device 1 or the second display device 2 in the extended display manner, to the second image. Specifically the third switch signal is an instruction signal for establishing communication with the communication part 41 of the second information processing device 4 and the first and second display devices 1 and 2.

Figure 5:
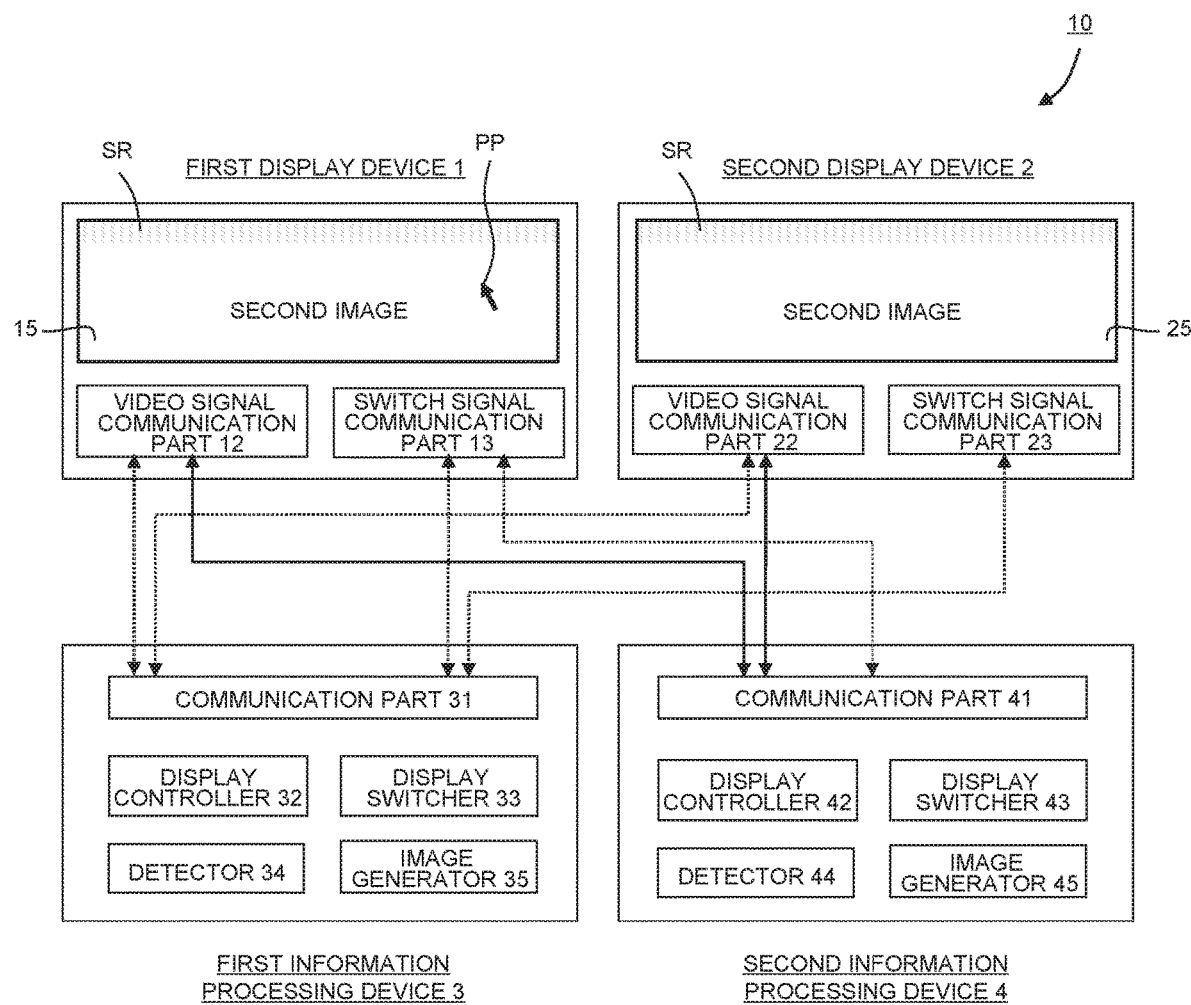
FIG. 5 is a schematic diagram showing a state that the second image is displayed on the first and second display devices 1 and 2 in the extended display manner.

Then, in S4, when the first and second display devices 1 and 2 receive the third switch signal, the first and second display devices 1 and 2 display the second image output from the second information processing device 4 in the extended display manner as shown in FIG. 5.

Thus, the processing in S3 and S4 is the first switch processing. That is, the first switching processing is a switch processing that switches the image, displayed on the first and second display devices 1 and 2 in the extended display manner, from the image of the first information processing device 3 to the image of the second information processing device 4. In the first switch processing of the present embodiment, the first switch processing is executed by outputting the third switch signal from the first information processing device 3 to the first and second display devices 1 and 2.

Figure 6:
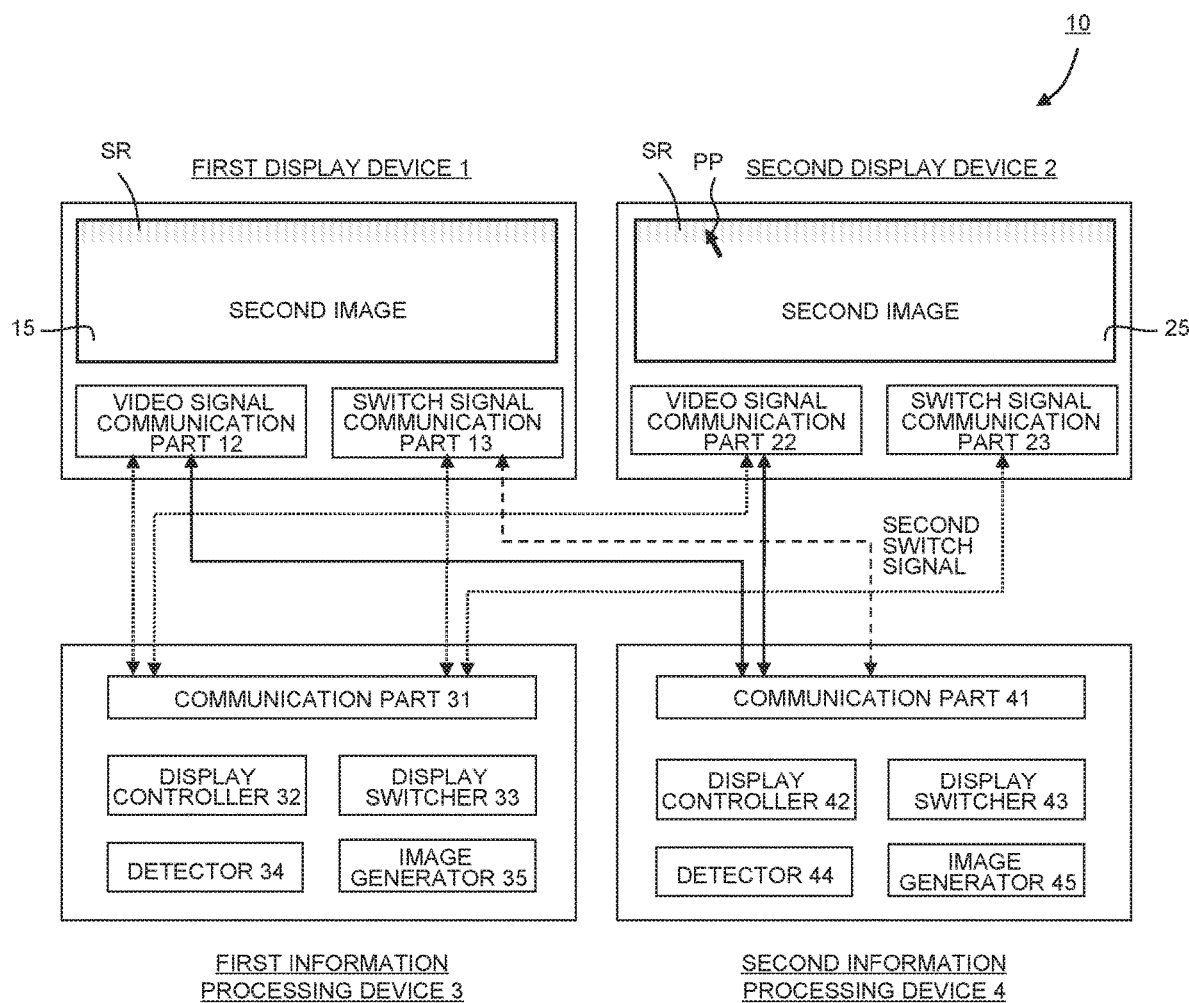
FIG. 6 is a schematic diagram showing a state that the second information processing device 4 outputs a second switch signal to the first display device 1. Here, the second switch signal is a signal for switching an image displayed on the first display device 1.

Next, as shown in FIG. 6, when the operation device 5 is operated to move the pointing position PP into the switch area SR, the detector 44 detect that the pointing position PP is positioned on the switch area SR in S5 of FIG. 2. Then, when the pointing position PP is detected by the detector 44, the display system 10 starts to execute the second switch processing. When the detector 44 does not detect the presence of the pointing position PP on the switch area SR, the processing returns to S4.

Figure 7:
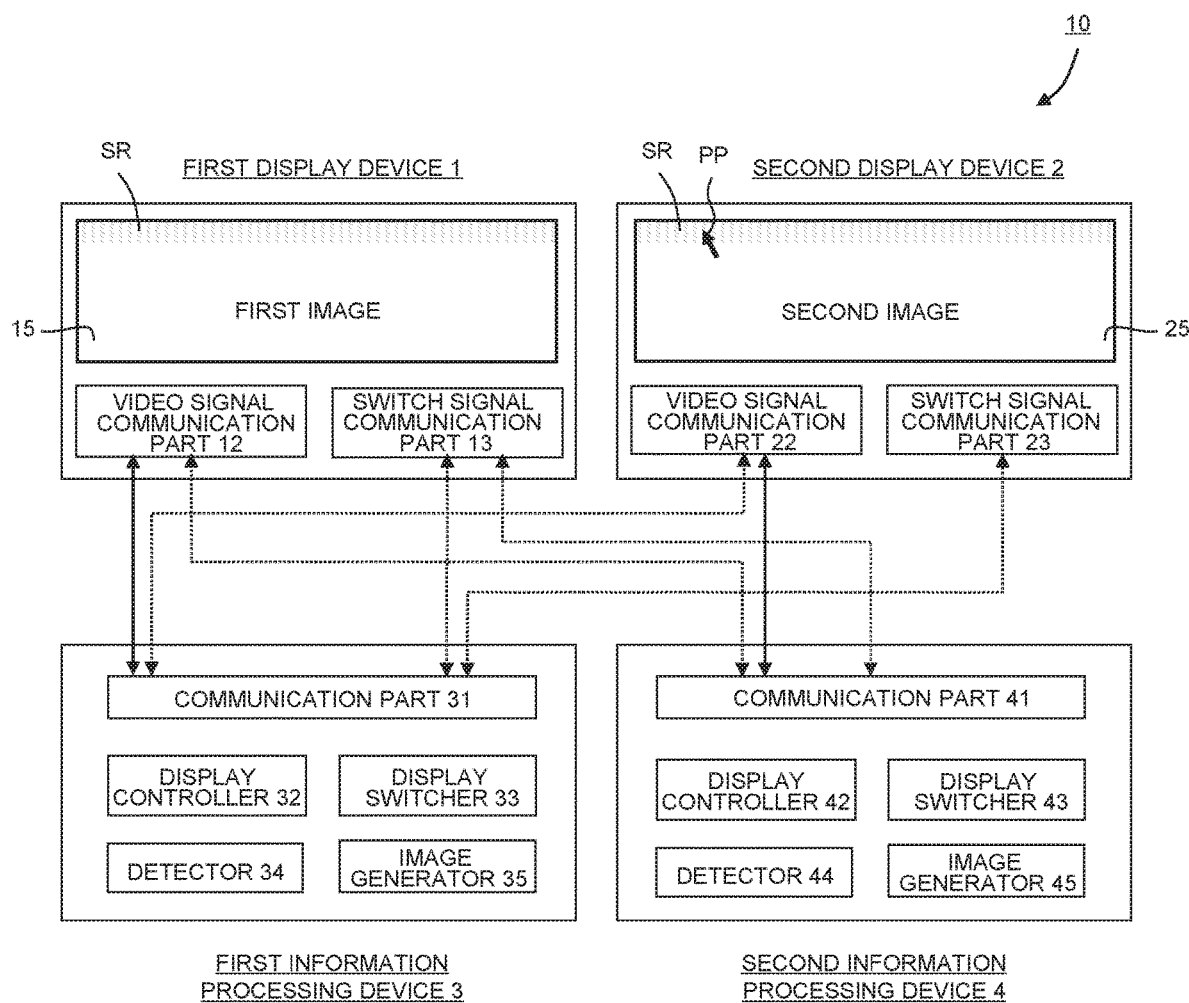
FIG. 7 is a schematic diagram showing a state that the first image is displayed on the first display device and the second image is displayed on the second display device.

Next, in S6, the second switch signal is transmitted from the second information processing device 4 to the first display device 1 as shown in FIG. 6. Here, the second switch signal is a signal for switching the image, displayed on the first display device 1, to the first image. Then, the communication part 41 of the second information processing device 4 and the switch signal communication part 23 of the second display device 2 are not connected, so the second information processing device 4 cannot send the second switch signal to the second display device 2. Thus, as shown in FIG. 7, the first image is displayed on the first display device 1 and the second image is displayed on the second display device 2.

Next, in S7, the first information processing device 3 detects the switching of the image of the first display device 1. In the present embodiment, the first information processing device 3 detects, via the video signal communication part 12 of the first display device 1, whether the image displayed on the first display device 1 has been switched.

Figure 8:
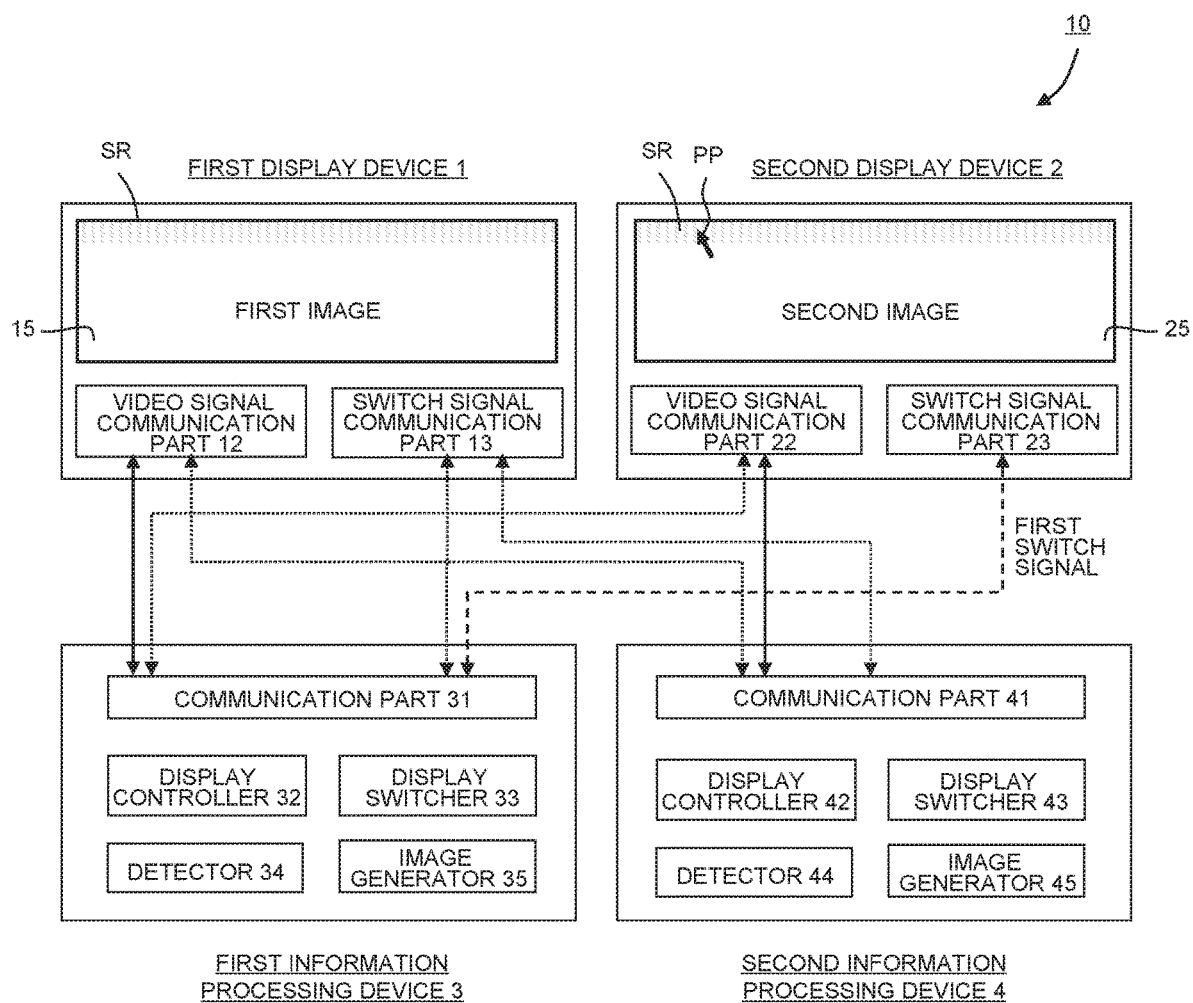
FIG. 8 is a schematic diagram showing a state that the first information processing device 3 outputs a first switch signal in response to the second switch signal. Here, the first switch signal is a signal for switching an image displayed on the second display device.

Next, in S8, the first switch signal is transmitted from the first information processing device 3 to the second display device 2 as shown in FIG. 8. Here, the first switch signal is a signal for switching the image, displayed on the second display device 2, to the first image. As described above, in this embodiment, when the image displayed on the first display device 1 is switched, the first information processing device 3 outputs the first switch signal to the second display device 2 so that the second display device 2 displays the image (the first image) output from the first information processing device 3.

Here, instead of the processing in S7, the first information processing device 3 may detect that the second signal has been output from the second information processing device 4 by using the switch signal communication part 13 of the first display device 1. Specifically, the first information processing device 3 may be configured to detect, via the switch signal communication part 13 of the first display device 1, whether the image displayed on the first display device 1 has been switched. For example, when the first display device 1 receives the second switch signal, the switch signal communication part 13 of the first display device 1 transmits a signal indicating that the second switch signal has been received by the first display device 1, to the first information processing device 3.

Further, instead of the processing in S7, the first information processing device 3 may detect that the second switch signal has been output from the second information processing device 4 by using the switch signal transfer part 14 of the first display device 1. Specifically, the switch signal transfer part 14 of the first display device 1 transfers the second switch signal, input from the second information processing device 4, to the first information processing device 3. Or, when the second switch signal is input from the second information processing device 4, the switch signal transfer part 14 of the first display device 1 outputs a signal, indicating that the second switch signal has been input, to the first information processing device 3. And the first information processing device 3 may be configured to, when the first information processing device 3 receives the signal output from the switch signal transfer part 14, output the first switch signal to the second display device 2.

Further, instead of the processing in S7, the first information processing device 3 may detect that the second signal has been output from the second information processing device 4 by using the operation device 5. Specifically, the first information processing device 3 may be configured to detect whether the image displayed on the first display device 1 has been switched by detecting that the operation device 5 has switched to a state in which the operation device is capable of operating the first information processing device 3.

Then, in S9, when the second display device 2 receives the first switch signal, the second display device 2 displays the image (the first image) of the first information processing device 3. Thus, the state of the display system 10 returns to the state shown in FIG. 3 again. In this way, the processing from S6 to S9 is the second switch processing. That is, the second switch processing is a switch processing that switches the image, displayed on the first and second display devices 1 and 2 in the extended display manner, from the image of the second information processing device 4 to the first information processing device 3. In the present embodiment, the second switch processing is executed by outputting the first switch signal from the first information processing device 3 to the second display device 2 after the second information processing device 4 outputs the second switch signal to the first display device 1 and the first display device 1 receives the second switch signal from the second information processing device 4.

Here, in FIGS. 3 to 8, the display switcher 33 or the display switcher 43 may display information, on at least one of the first and second display devices 1 and 2, indicating which image output from the first information processing device 3 or the second information processing device 4 is displayed on the first and second display devices 1 and 2 in the extended display manner. The first display device 1 or the second display device 2 may be configured to display an electrical health record.

As described above, in the display system 10 according to the first embodiment, the second information processing device 4 is configured to output the second switch signal for switching the image displayed on the first display device 1 to the first display device 1. Then, the first information processing device 3 is configured to output the first switch signal for switching the image displayed on the second display device 2 to the second display device 2 according to the second switch signal. Thus, even if the switch signal communication part 23 of the second display device 2 and the communication part 41 of the second information processing device 4 cannot communicate the switch signal with one another, the display system 10 can control a plurality of the display devices.

2. Second Embodiment

Figure 9:
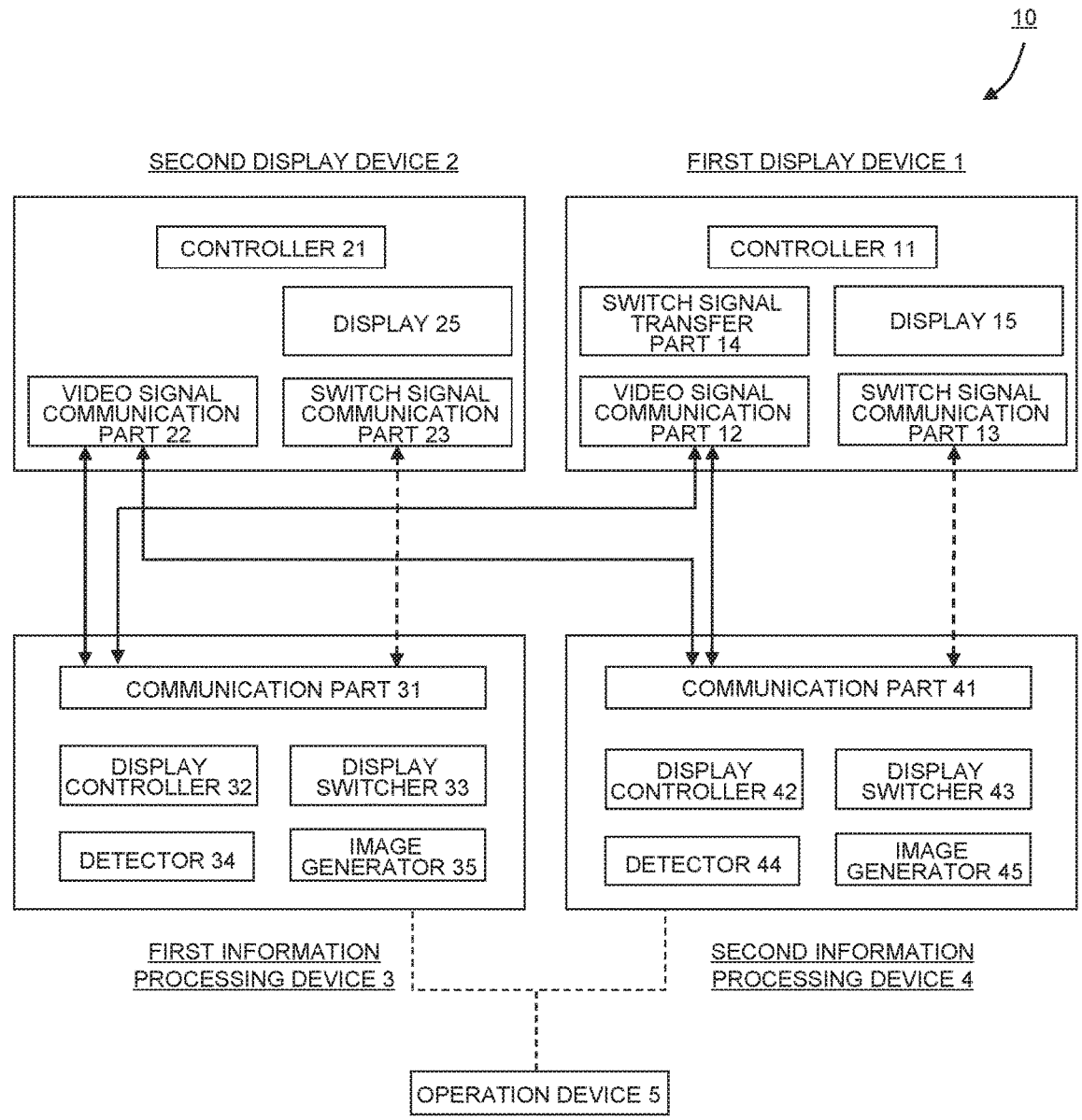
FIG. 9 is a functional block diagram showing a configuration of the display system 10 according to a second embodiment of the present invention.

Hereinafter, the display system 10 according to the second embodiment of the present invention will be described with reference to FIGS. 9 to 19. As shown in FIG. 9, unlike the first embodiment, the second embodiment includes the first and second display devices 1 and 2 each including one switch signal communication part 13 and one switch signal communication part 23. Then, the switch signal communication part 13 of the first display device 1 is configured to communicate with the communication part 41 of the second information processing device 4, and the switch signal communication part 23 of the second display device 2 is configured to communicate with the communication part 31 of the first information processing device 3.

In the display system 10 according to the second embodiment, the operation device 5 is communicably connected to the first and second information processing devices 3 and 4. In this embodiment, the operation device 5 and the first and second information processing devices 3 and 4 are connected by wireless communication such as Bluetooth (registered trademark). When the image displayed on the first and second display devices 1 and 2 in the extended display manner is the first image, the operation device 5 establishes a pairing with the first information processing device 3, and the operation device 5 is capable of operating the first information processing device 3. On the other hand, when the image displayed on the first and second display devices 1 and 2 in the extended display manner is the second image, the operation device 5 establishes the pairing with the second information processing device 4, and the operation device 5 is capable of operating the second information processing device 4.

2-1. Flowchart of Second Embodiment
<First Switch Processing>

Figure 10:
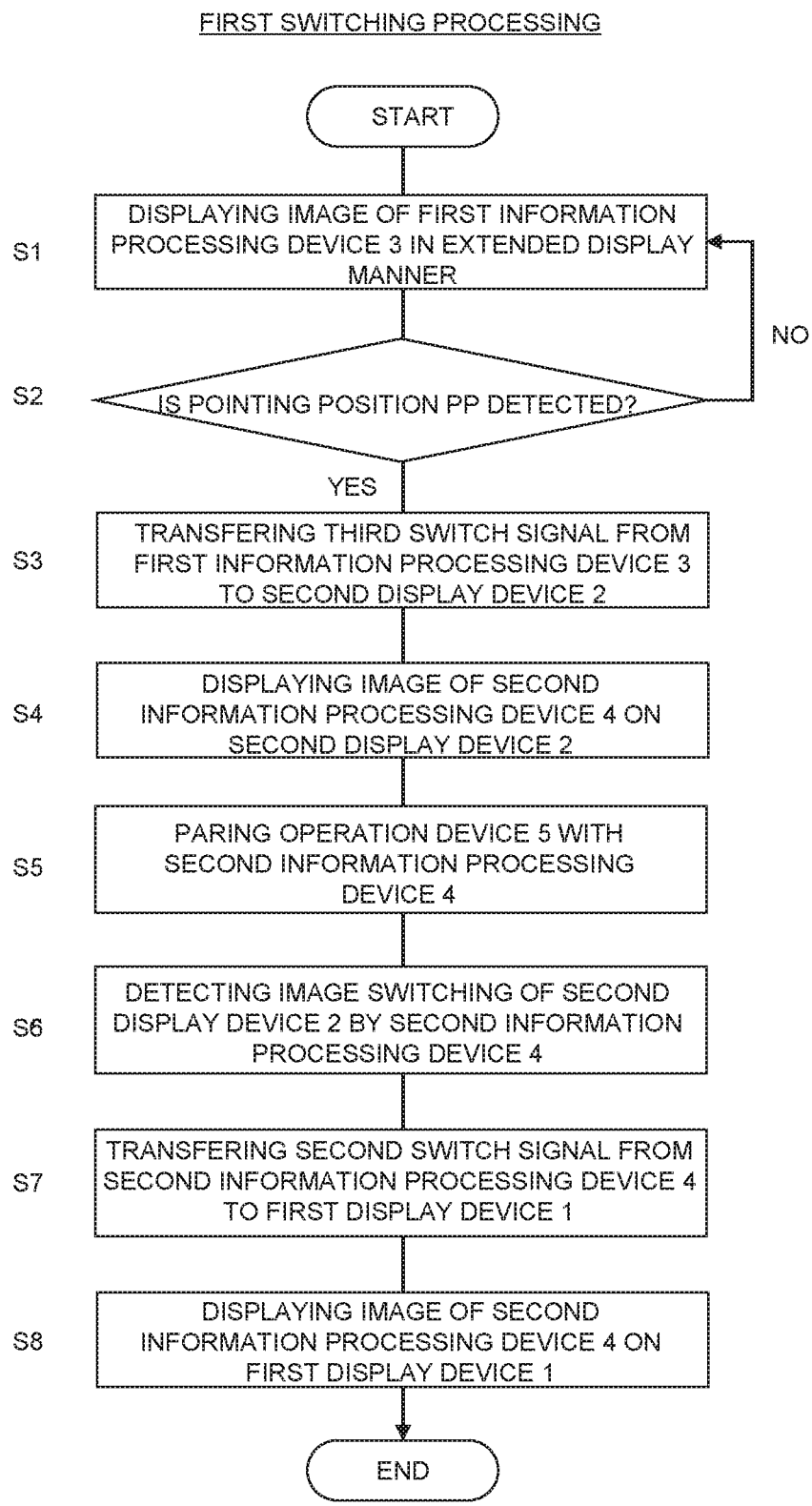
FIG. 10 is a flowchart showing first switch processing of the display system 10 according to the second embodiment.

As shown in FIG. 10, in S1, the first and second display devices 1 and 2 included in the display system 10 perform the extended display of the image (the first image) output from the first information processing device 3. This corresponds to the situation in FIG. 12. Then, the operation device 5 has established the pairing with the first information processing device 3, and the operation device 5 is capable of operating the first information processing device 3.

Figure 13:
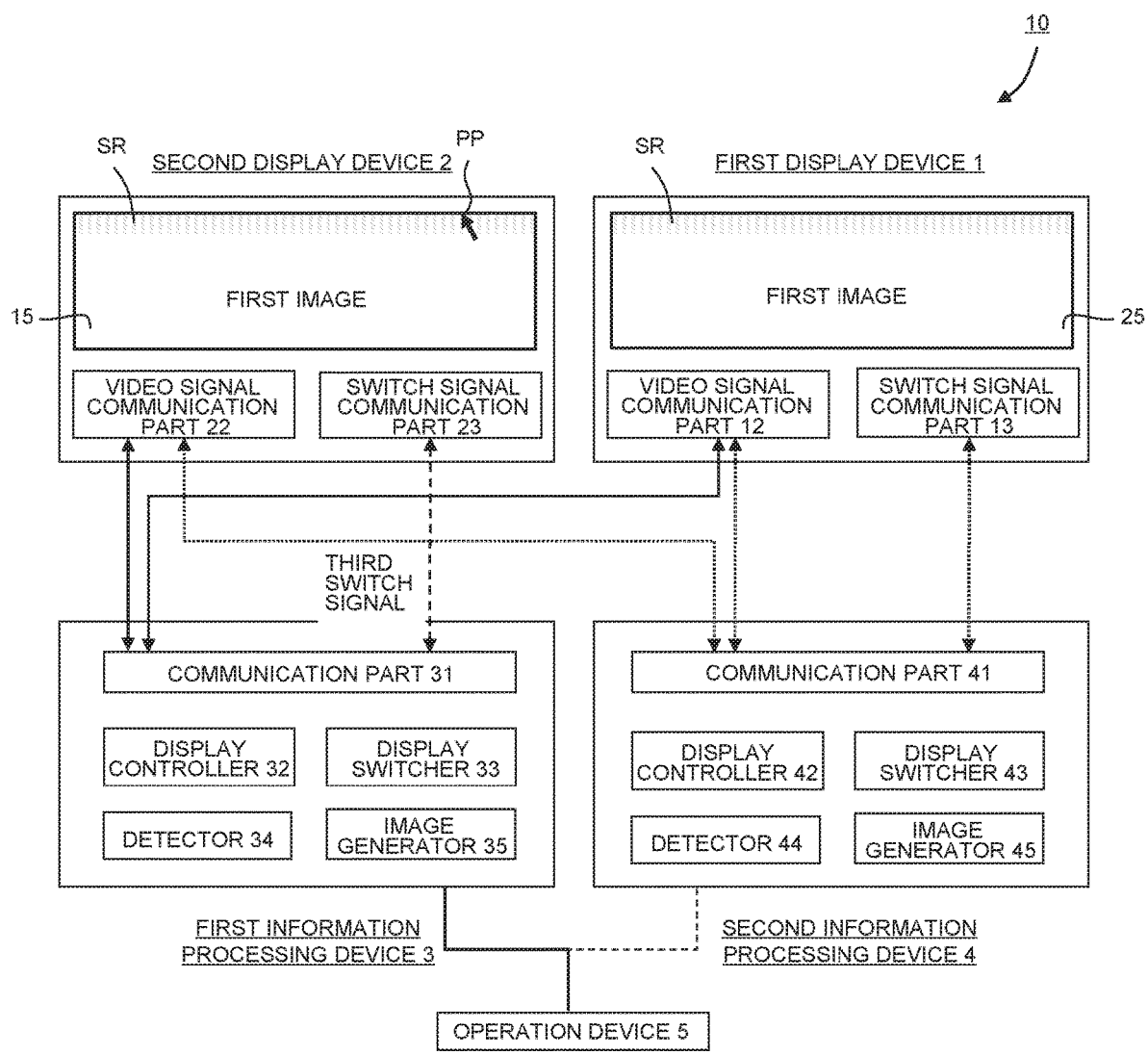
FIG. 13 is a schematic diagram showing a state that the first information processing device 3 outputs the third switch signal to the second display device 2.

Next, as shown in FIG. 13, when the operation device 5 is operated to move the pointing position PP into the switch area SR, the detector 34 detects that the pointing position PP is positioned on the switch area SR in S2 of FIG. 10. Then, when the pointing position PP is detected by the detector 34, the display system 10 starts to execute the first switch processing. When the detector 34 does not detect the presence of the pointing position PP on the switch area SR, the processing returns to S1.

Next, in S3, the third switch signal is transmitted from the first information processing device 3 to the second display device 2 as shown in FIG. 13. Here, the third switch signal is the signal for switching the image displayed on the second display device 2 to the second image.

Figure 14:
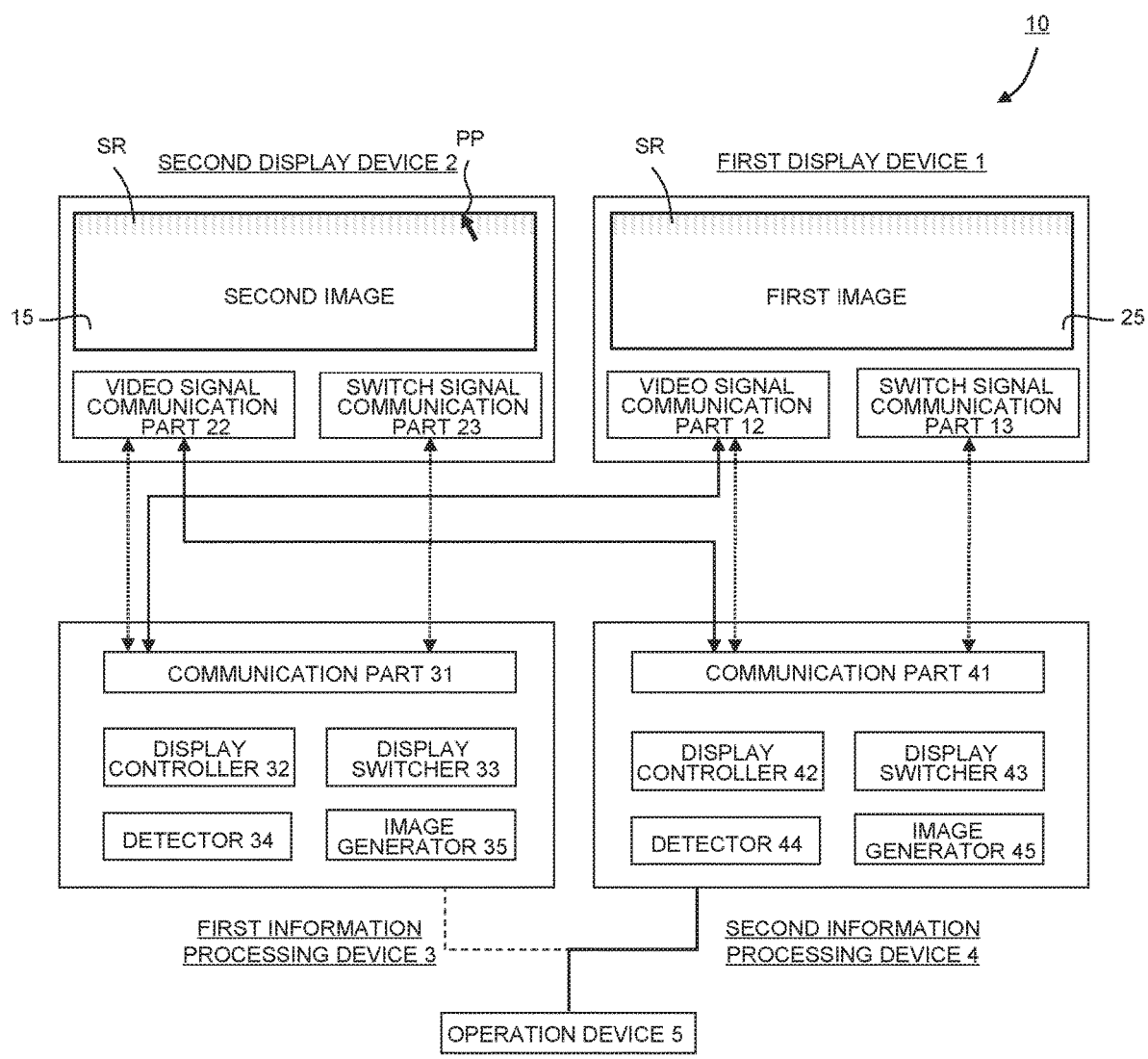
FIG. 14 is a schematic diagram showing a state that the first image is displayed on the first display device and the second image is displayed on the second display device.

Then, in S4, when the second display device 2 receives the third switch signal, the second display device 2 displays the second image output from the second information processing device 4 as shown in FIG. 14.

Next, in S5, the pairing of the operation device 5 and the first information processing device 3 is released, and the operation device 5 establishes the pairing with the second information processing device 4, thus the information device that can be operated by the operation device 5 is switched from the first information processing device 3 to the second information processing device 4.

Next, in S6, the second information processing device 4 detects the switching of the image of the second display device 2. In the present embodiment, the second information processing device 4 detects, via the video signal communication part 22 of the second display device 2, whether the image displayed on the second display device 2 has been switched. Note that S5 may be executed after S6.

Figure 15:
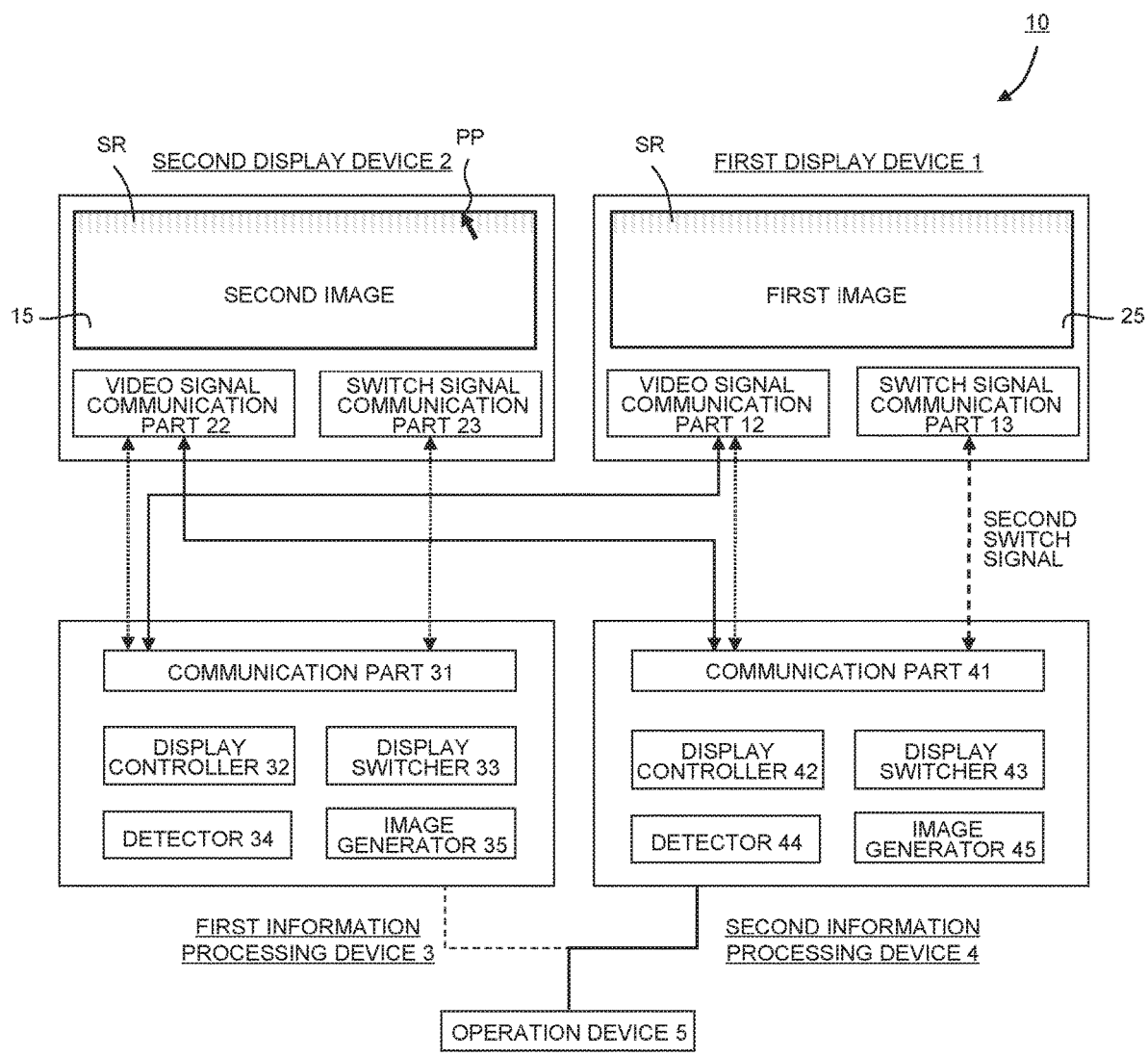
FIG. 15 is a schematic diagram showing a state that the second information processing device 4 outputs the second switch signal in response to the third switch signal.
Figure 16:
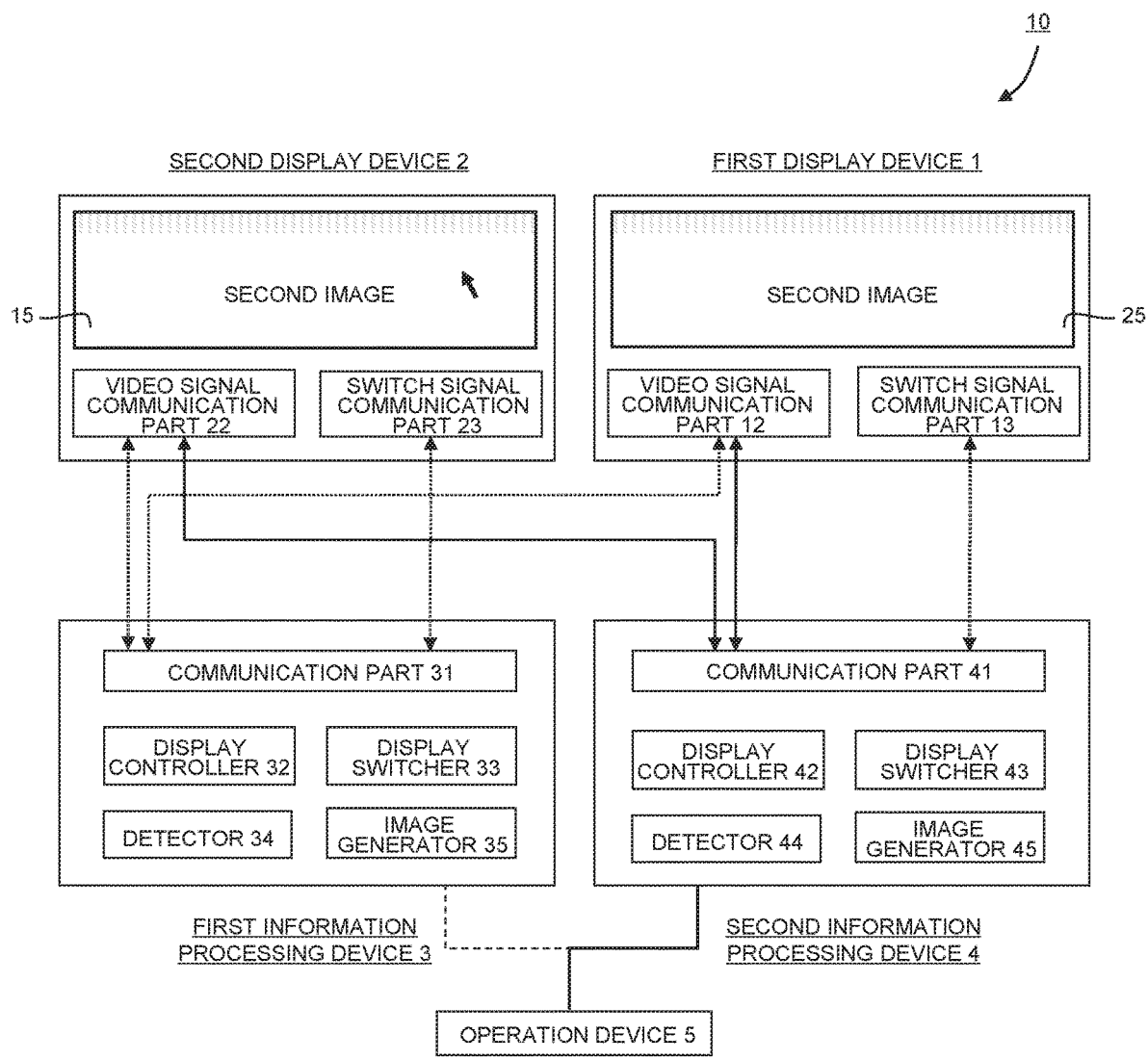
FIG. 16 is a schematic diagram showing a state that the second image is displayed on the first and second display devices 1 and 2 in the extended display manner.

Next, in S7, the second switch signal is transmitted from the second information processing device 4 to the first display device 1 as shown in FIG. 15. Here, the second switch signal is the signal for switching the image displayed on the first display device 1 to the second image. In this way, in the present embodiment, when the image displayed on the second display device 2 is switched, the second information processing device 4 outputs the second switch signal to the first display so that the first display device 1 displays the image (the second image) output from the second information processing device 4.

Then, in S8, when the first display device 1 receives the second switch signal, the first display device 1 displays the image (the second image) of the second information processing device 4. Thus, the state of the display system 10 becomes the state shown in FIG. 16.

<Second Switch Processing>

Next, the second switch processing, in which the images displayed in the first and second display devices 1 and 2 are switched from the second image to the first image, will be described.

Figure 11:
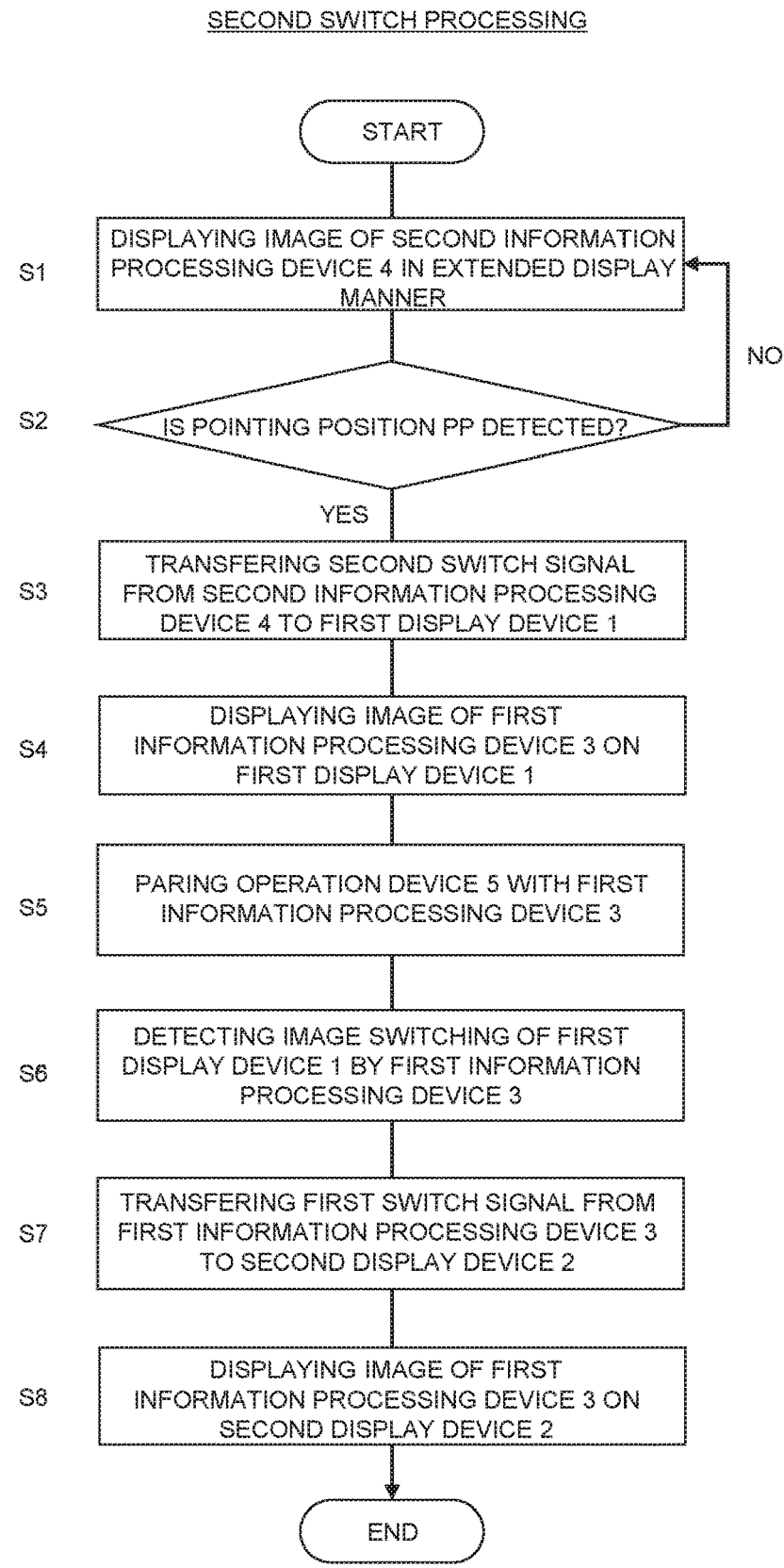
FIG. 11 is a flowchart showing second switch processing of the display system 10 according to the second embodiment.
Figure 12:
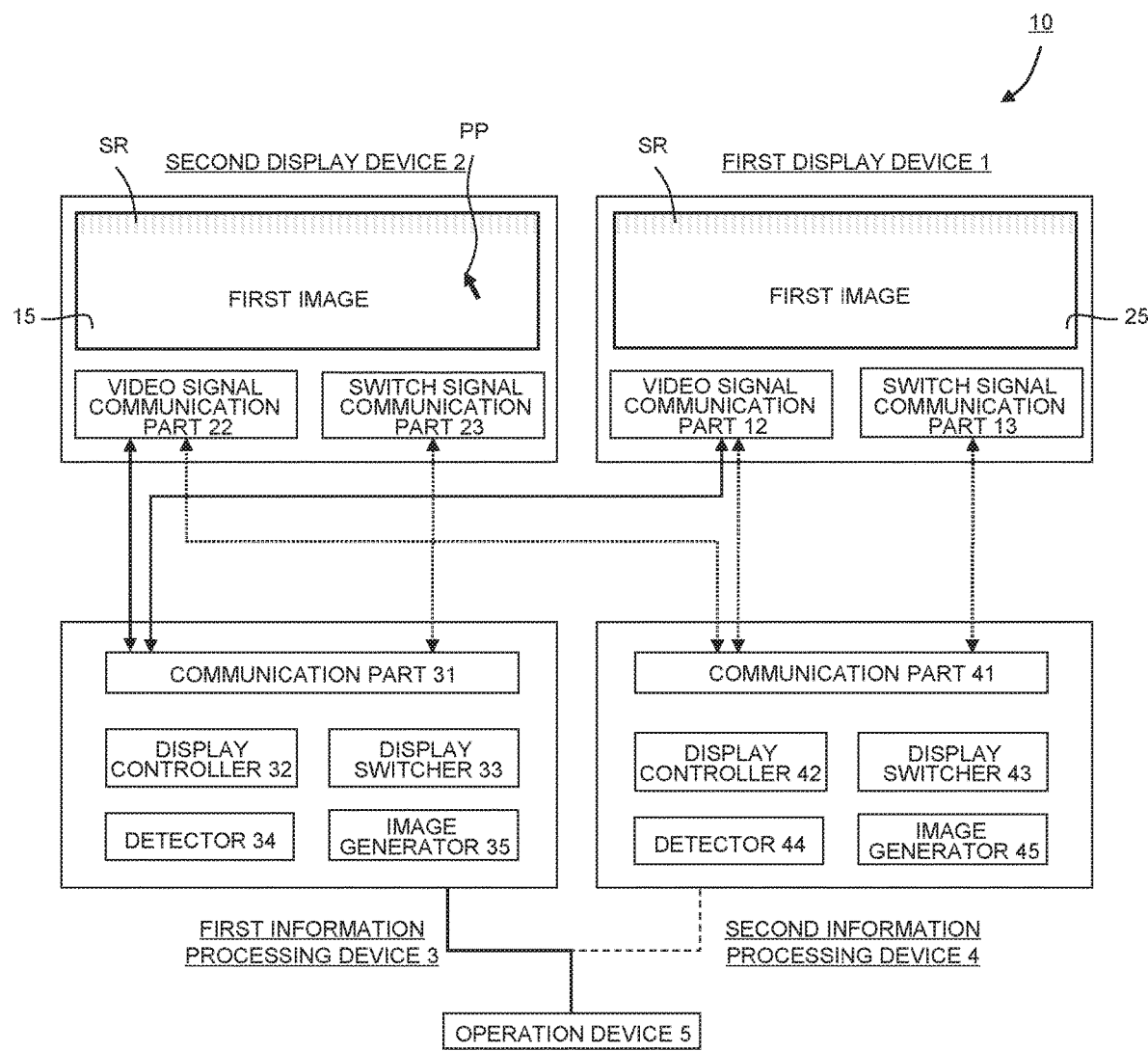
FIG. 12 is a schematic diagram showing a state that the first image is displayed on the first and second display devices 1 and 2 in the extended display manner.

As shown in FIG. 11, in S1, the first and second display devices 1 and 2 included in the display system 10 perform the extended display with respect to the image (the second image) output from the second information processing device 4. This corresponds to the state in FIG. 16. Then, the operation device 5 establishes the pairing with the second information processing device 4, and the operation device 5 is capable of operating the second information processing device 4

Figure 17:
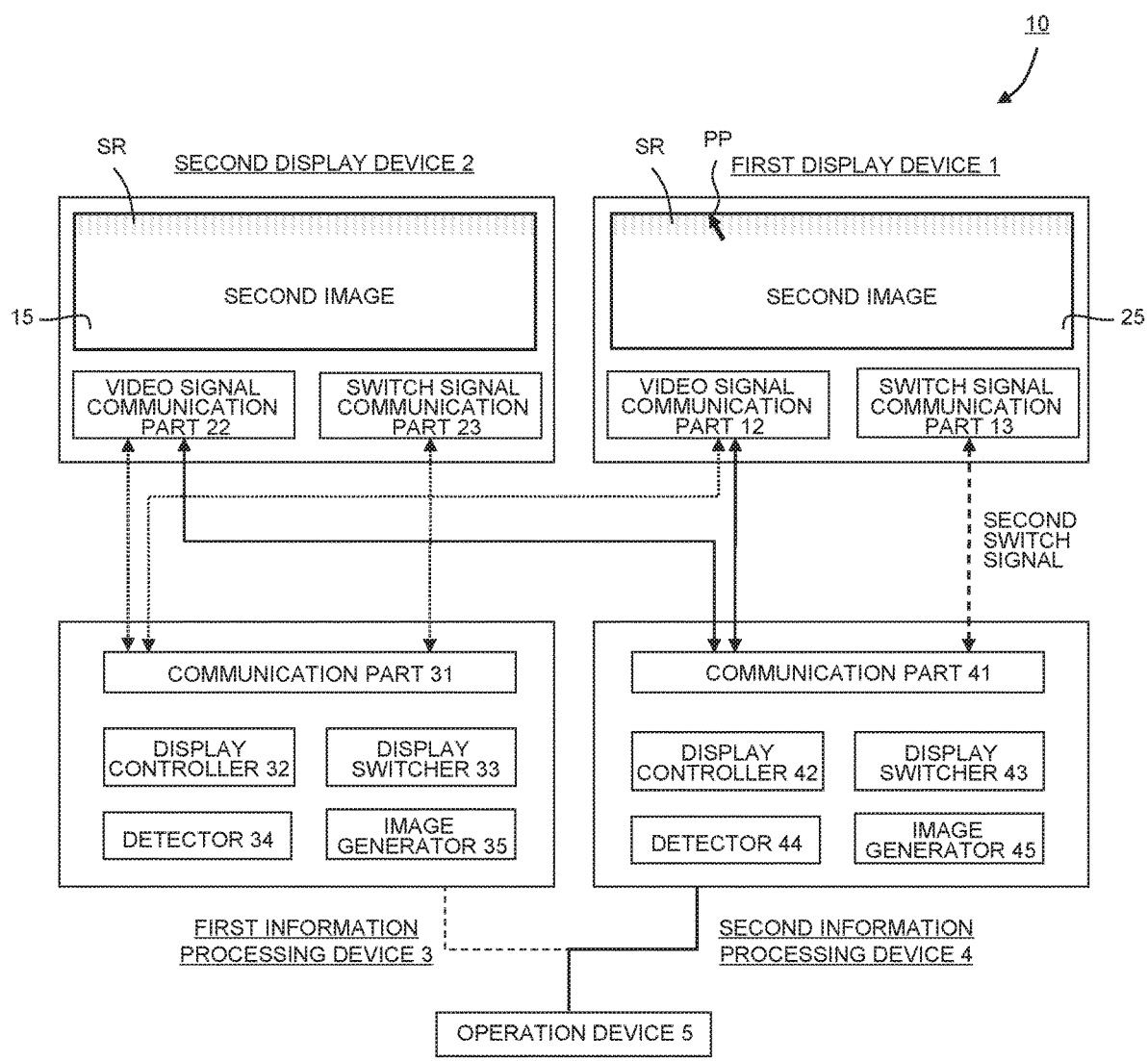
FIG. 17 is a schematic diagram showing a state that the second information processing device 4 outputs the second switch signal to the first display device 1.

Next, as shown in FIG. 17, when the operation device 5 is operated to move the pointing position PP into the switch area SR, the detector 44 detects that the pointing position PP is positioned on the switch area SR in S2 of FIG. 11. Then, when the pointing position PP is detected by the detector 44, the display system 10 starts to execute the second switch processing. When the detector 44 does not detect the presence of the pointing position PP on the switch area SR, the processing returns to S1.

Next, in S3, the second switch signal is transmitted from the second information processing device 4 to the first display device 1 as shown in FIG. 17. Here, the second switch signal is the signal for switching the image displayed on the first display device 1 to the first image.

Figure 18:
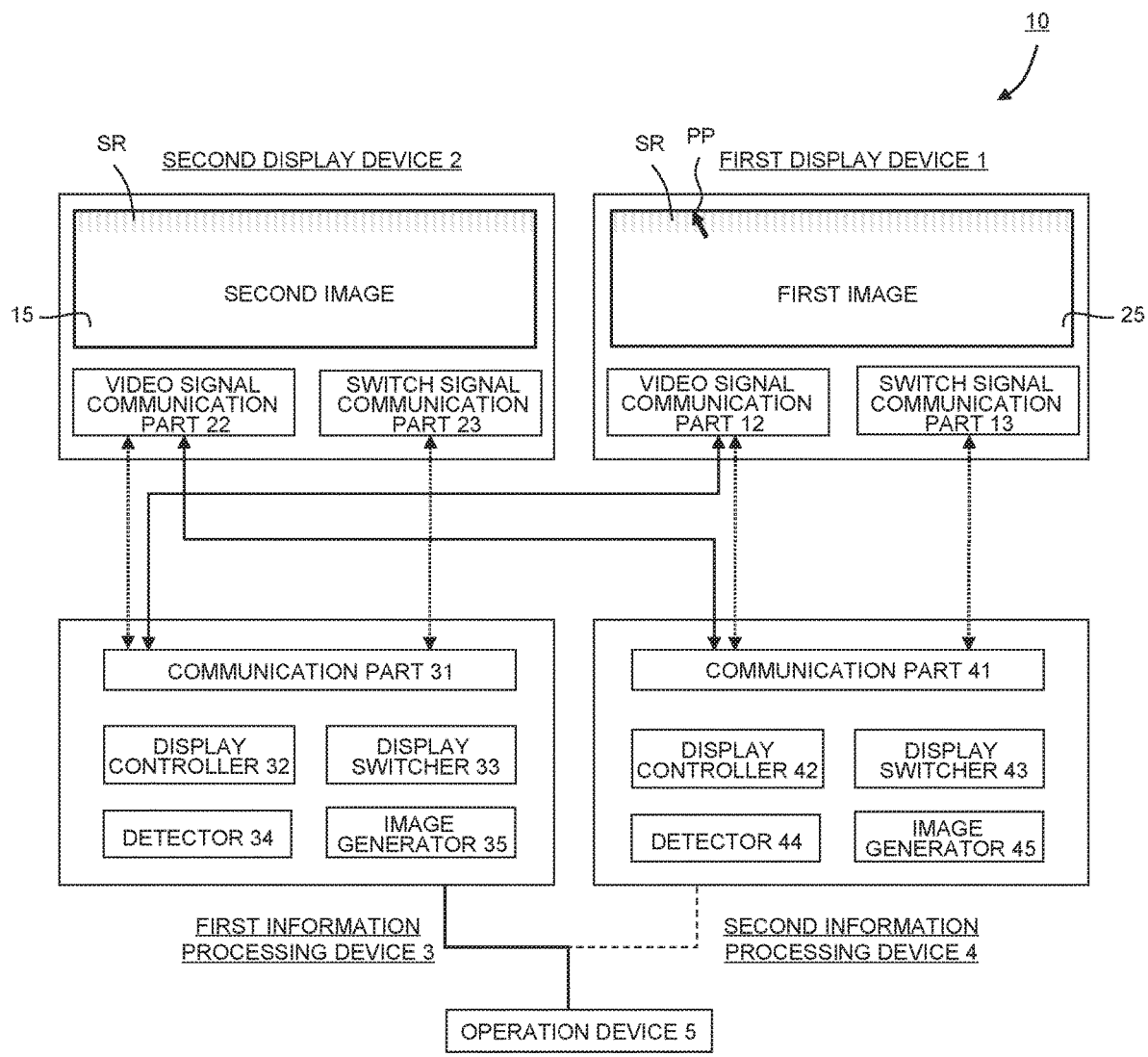
FIG. 18 is a schematic diagram showing a state that the first image is displayed on the first display device and the second image is displayed on the second display device.

Then, in S4, when the first display device 1 receives the second switch signal, the first display device 1 displays the first image output from the first information processing device 3 as shown in FIG. 18.

Next, in S5, the pairing of the operation device 5 and the second information processing device 4 is released, and the operation device 5 establishes the pairing with the first information processing device 3, thus the information device that can be operated by the operation device 5 is switched from the second information processing device 4 to the first information processing device 3.

Next, in S6, the first information processing device 3 detects the switching of the images of the first display device 1. In this embodiment, the first information processing device 3 detects, via the video signal communication part 12 of the first display device 1, whether the image displayed on the first display device 1 has been switched. Note that S5 may be executed after S6.

Figure 19:
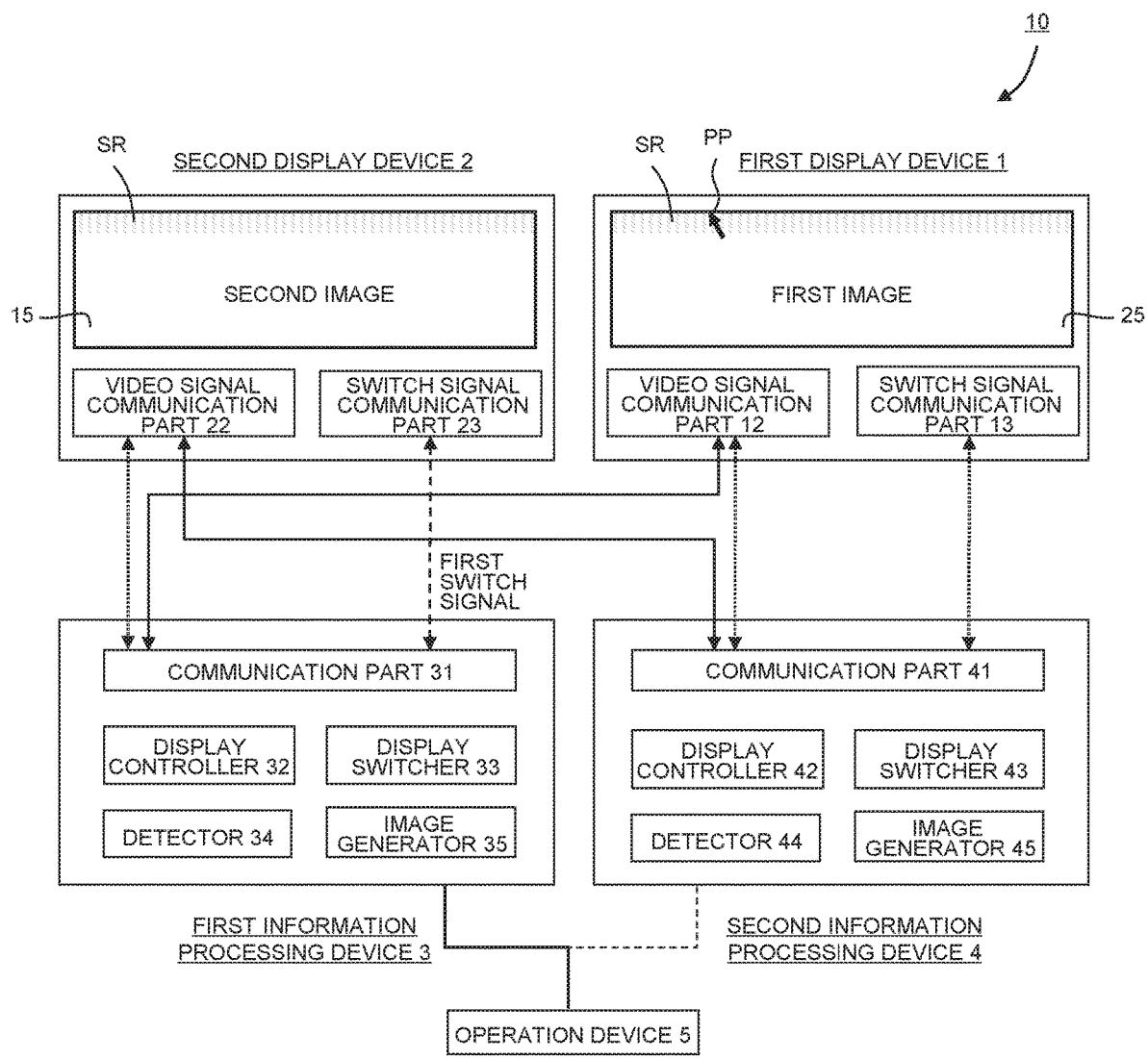
FIG. 19 is a schematic diagram showing a state that the first information processing device 3 outputs the first switch signal in response to the second switch signal.

Next, in S7, the first switch signal is transmitted from the first information processing device 3 to the second display device 2 as shown in FIG. 19. Here, the first switch signal is the signal for switching the image displayed on the second display device 2 to the first image. In this way, in this embodiment, when the image displayed on the first display device 1 is switched, the first information processing device 3 outputs the first switch signal so that the second display device 2 displays the image (the first image) output from the first information processing device 3.

Then, in S8, when the second display device 2 receives the first switch signal, the second display device 2 displays the image (the first image) of the first information processing device 3. Thus, the state of the display system 10 returns to the state shown in FIG. 12 again.

As described above, the display system 10 according to the second embodiment can control the plurality of the display devices even in the case that the switch signal communication part 13 of the first display device 1 and the switch signal communication part 23 of the second display device 2 each has only one port and can communicate with only one of the first information processing device 3 and the second information processing device 4.

4. Another Embodiment

Although various embodiments have been described above, the present invention is not limited to these.

For example, each component of the first information processing device 3 or the second information processing device 4 may be incorporated when the first information processing device 3 or the second information processing device 4 is manufactured. Or, each component of the first information processing device 3 or the second information processing device 4 may be realized by an application downloaded via the Internet after the shipment of the first information processing device 3 or the second information processing device 4.

The embodiment according to the present invention is also realized with following configurations.

A program causing a computer to function as a controller that controls a display system including first and second information processing devices and first and second display devices, the first and second display devices being configured to perform extended display with respect to one of an image output from the first information processing device and an image output from the second information processing device, the second information processing device being configured to output a second switch signal for switching an image displayed on the first display device to the first display device, the program comprising:

outputting, when the second switch signal is output from the second information processing device to the first display device and the image displayed on the first display device is switched, a first switch signal for switching an image displayed on the second display device from the first information processing device to the second display device.

Further, the embodiment of the present invention is also realized with a configuration that above program is stored in a non-transitory computer readable medium.

DESCRIPTION OF REFERENCE SIGNS 1 first display device
2 second display device
3 first information processing device
4: second information processing device
5 operation device
10 display system
11 controller
12 video signal communication part
13 switch signal communication part
14 switch signal transfer part
15 display
21 controller
22 video signal communication part
23 switch signal communication part
25 display
31 communication part
32 display controller
33 display switcher
34 detector
35 image generator
41 communication part
42 display controller
43 display switcher
44 detector
45 image generator
PP pointing position
SR switch area

The invention claimed is:

1. A display system comprising:
first and second information processing devices; and
first and second display devices, wherein
the first and second display devices are configured to perform extended display with respect to one of an image output from the first information processing device and an image output from the second information processing device,
the second information processing device is configured to output a second switch signal for switching an image displayed on the first display device to the first display device, and
the first information processing device is configured to, when the second switch signal is output from the second information processing device to the first display device and the image displayed on the first display device is switched, output a first switch signal for switching an image displayed on the second display device to the second display device.

2. The display system of claim 1, wherein the first information processing device, when the second switch signal is output from the second information processing device to the first display device and the image displayed on the first display device is switched, outputs the first switch signal to the second display so that the second display displays the image output from the first information processing device.

3. The display system of claim 2, wherein the first and second displays include video signal communication parts respectively,
the video signal communication parts are configured to communicate a video signal with between the first and second information processing devices, and
the first information processing device is configured to detect, via the video signal communication part of the first display device, whether the image displayed on the first display device has been switched.

4. The display system of claim 1, wherein the first and second display devices include switch signal communication parts respectively,
the switch signal communication parts are configured to communicate the first switch signal or the second switch signal with at least one of the first and second information processing device, and
the first information processing device is configured to detect, via the switch signal communication part of the first display device, whether the image displayed on the first display device has been switched.

5. The display system of claim 4, wherein the first display device includes a switch signal transfer part,
the switch signal transfer part is configured to transfer the second switch signal, input from the second information processing device to the first display device, to the first information processing device, or
output an output signal to the first information processing device when the second switch signal is input from the second information processing device to the first display device, the output signal indicating that the second switch signal is input from the second information processing device to the first display device, and;
the first information processing device outputs the first switch signal to the second display device when the first information processing device receives the second switch signal or the output signal from the switch signal transfer part.

6. The display system of claim 1, further comprising:
an operation device configured to operate one of the first and second information processing devices that outputs the image to the first and second display devices, wherein
the first information processing device is configured to detect whether the image displayed on the first display device has been switched by detecting that the operation device has switched to a state in which the operation device is capable of operating the first information processing device.

7. The display system of claim 1, wherein the first and second display devices include switch signal communication parts respectively,
the switch signal communication parts are configured to communicate the first switch signal or the second switch signal with at least one of the first and second information processing device,
the switch signal communication part of the first display device is configured to communicate with the first and second information processing devices,
the switch signal communication part of the second display device is configured to communicate with the first information processing device,
the first switch processing, which switches the image displayed on the second display device from an image of the first information processing device to an image of the second information processing device, is executed when the first information processing device outputs a third switch signal to the first and second display devices, and the second switch processing, which switches the image displayed on the first display device from the image of the second information processing device to the image of the first information processing device, is executed when the first information processing device outputs the first switch signal to the second display device after the first display device receives the second switch signal from the second information processing device.

8. The display system of claim 1, further comprising:
an operation device configured to operate one of the first and second information processing devices that outputs the image to the first and second display devices.

9. The display system of claim 8, wherein the operation device is connected to the first display device.

10. The display system of claim 8, wherein the operation device is configured to indicate a pointing position on the first and second display devices.

11. The display system of claim 10, further comprising:
a detector configured to, when the image is displayed on the first and second display devices, detect whether the pointing position is positioned on a switch area arranged in a direction perpendicular to a direction in which the first and second display devices are arranged, wherein
the first switch processing or the second switch processing is executed when the detector detects the pointing position on the switch area.

12. The display system of claim 1, wherein the first and second information processing devices include display switchers respectively, each of the display switchers displays information on at least one of the first and second display devices,
the information indicating which image output from the first information processing device or the second information processing device is displayed on the first and second display devices.

13. The display system of claim 1, wherein the first display device or the second display device is configured to display an electrical health record.

14. A non-transitory computer readable medium that stores a program causing a computer to function as a controller that controls a display system including first and second information processing devices and first and second display devices, the first and second display devices being configured to perform extended display with respect to one of an image output from the first information processing device and an image output from the second information processing device, the second information processing device being configured to output a second switch signal for switching an image displayed on the first display device to the first display device, the program comprising:
outputting, when the second switch signal is output from the second information processing device to the first display device and the image displayed on the first display device is switched, a first switch signal for switching an image displayed on the second display device from the first information processing device to the second display device.

* * * * *